(12) United States Patent
Sun et al.

(10) Patent No.: US 10,836,777 B2
(45) Date of Patent: Nov. 17, 2020

(54) METHOD FOR PREPARING 2-(CYCLOHEXENYLIDENE) MALONIC ACID DERIVATIVES AND USES THEREOF

(71) Applicant: ORIENTAL(LUZHOU) AGROCHEMICALS. CO., LTD, Sichuan (CN)

(72) Inventors: Yinwei Sun, Sichuan (CN); Zhongyuan Wang, Sichuan (CN); Pan Zhang, Sichuan (CN); Bangchi Chen, Sichuan (CN)

(73) Assignee: ORIENTAL(LUZHOU) AGROCHEMICALS. CO., LTD, Luzhou (CN)

( * ) Notice: Subject to any disclaimer, the term of this patent is extended or adjusted under 35 U.S.C. 154(b) by 0 days.

(21) Appl. No.: 16/439,679

(22) Filed: Jun. 12, 2019

(65) Prior Publication Data

US 2019/0292200 A1   Sep. 26, 2019

Related U.S. Application Data

(63) Continuation of application No. PCT/CN2016/113671, filed on Dec. 30, 2016.

(51) Int. Cl.
| | |
|---|---|
| *C07D 498/04* | (2006.01) |
| *C07C 55/28* | (2006.01) |
| *C07C 13/20* | (2006.01) |
| *C07C 67/22* | (2006.01) |
| *C07C 67/30* | (2006.01) |
| *C07C 69/38* | (2006.01) |
| *C07C 255/31* | (2006.01) |
| *C07C 253/30* | (2006.01) |
| *C07C 255/33* | (2006.01) |
| *C07C 253/34* | (2006.01) |
| *C07C 69/612* | (2006.01) |
| *A01N 43/90* | (2006.01) |

(52) U.S. Cl.
CPC .......... *C07D 498/04* (2013.01); *A01N 43/90* (2013.01); *C07C 13/20* (2013.01); *C07C 55/28* (2013.01); *C07C 67/22* (2013.01); *C07C 67/30* (2013.01); *C07C 69/38* (2013.01); *C07C 69/612* (2013.01); *C07C 253/30* (2013.01); *C07C 253/34* (2013.01); *C07C 255/31* (2013.01); *C07C 255/33* (2013.01)

(58) Field of Classification Search
None
See application file for complete search history.

(56) References Cited

FOREIGN PATENT DOCUMENTS

| CN | 1355806 A | 6/2002 |
|---|---|---|
| CN | 102336686 A | 2/2012 |
| CN | 103804232 A | 5/2014 |

OTHER PUBLICATIONS

Zimmerman et al. "Molecular control of excited cross-conjugated triene rearrangements. Exploratory and mechanistic organic photochemistry" Journal of the American Chemical Society, 1979, vol. 101, No. 7, pp. 1841-1857.*
Ma, Chao et al. "A Concise Assembly of Electron-Deficient 2, 4-Dienes and 2, 4-Dienals: Regio-and Stereoselective Exo-Diels-Alder and Redox Reactions through Sequential Amine and Carbene Catalysis", Angewandte Chemie, 44 (22), Mar. 13, 2013 (Mar. 13, 2013), supporting information, pp. S3-S5.
Park, D.Y. et al. "Regioselective Synthesis of Pentasubstituted Benzene Derivatives: TBAF as an Effective Catalyst for the Sequential Michael Addition-intramolecular Aldolization", Tetrah日-dron Letters, vol. 47, Jul. 28, 2006 (Jul. 28, 2006), pp. 6641-6645, schemes 1-3, and table 1.
Barinelli, L.S. et al. "Deprotonation of the adducts of .beta.-dicarbonyl anions and [(.eta.4-diene)Co(CO)3]BF4" Organometallics, 8(10), Oct. 1, 1989 (Oct. 1, 1989), pp. 2474-2476, scheme II.
Volcho, K. P. et al. "Competing Michael and Knoevenagel Reactions of Terpenoids with Malononitrile on Basic Cs-beta Zeolite", Journal of Molecular Catalysis A: Chemical, 195 (1-2), Mar. 18, 2003 (Mar. 18, 2003, pp. 263-274, scheme 7, compound 25.

* cited by examiner

*Primary Examiner* — Joseph R Kosack
(74) *Attorney, Agent, or Firm* — Wayne & Ken, LLC; Tony Hom

(57) ABSTRACT

Disclosed are a method for preparing 2-(cyclohexenylidene) malonic acid derivatives and uses thereof. In this method, an olefin and a 2-substituted malonic acid derivative are used as starting materials to prepare the 2-(cyclohexenylidene) malonic acid derivative in the presence of a catalyst through cyclization reaction. This method has the following advantages: (1) the method can be very efficiently used for the synthesis of highly sterically-hindered 2-(2,6-disubstituted cyclohexenylidene) malonic acid derivatives; (2) the reaction yield is high, the reaction conditions are mild, and the wastes are less, favorable for industrial production. More importantly, the present invention extends the further use of 2-(cyclohexenylidene)malonic acid derivatives in organic synthesis, especially in the synthesis of 2-aryl malonic acid derivatives and their corresponding drugs such as Pinoxaden.

9 Claims, No Drawings

METHOD FOR PREPARING 2-(CYCLOHEXENYLIDENE) MALONIC ACID DERIVATIVES AND USES THEREOF

CROSS-REFERENCE TO RELATED APPLICATIONS

This application is a continuation of International Patent Application No. PCT/CN2016/113671, filed on Dec. 30, 2016. The content of the aforementioned application, including any intervening amendments thereto, is incorporated herein with reference in its entirety.

TECHNICAL FIELD

The application relates to organic synthesis, and specifically to a novel method for preparing 2-(cyclohexenylidene) malonic acid derivatives and uses thereof.

BACKGROUND 2-(Cyclohexenylidene) malonic acid derivatives are a class of organic compounds having multiple functional groups. There are two methods available for the preparation of such compounds (*J. Mol. Cata. A. Chem.* 2003, 195 (1-2), 263; *Organometallics* 1989, 8 (10), 2474).

In the first method, a cyclohexenone derivative is used as a starting material for preparing the 2-(cyclohexenylidene) malonic acid derivative (*J. Mol. Cata. A. Chem.* 2003, 195 (1-2), 263). The cyclohexenone derivative reacts with a malonic acid derivative through Knoevenagel condensation to produce the 2-(cyclohexenylidene) malonic acid derivative. Such method requires a highly active cyclohexenone. For less active 6-substituted cyclohexenone starting material, due to large steric hindrance, the yield of the Knoevenagel condensation is extremely low (3%). It is even a greater challenge to use this method for the preparation of 2-(2,6-disubstituted cyclohexenylidene) malonic acid derivatives using sterically more hindered 2,6-disubstituted cyclohexenone as the raw material.

In the second method, a cyclohexadiene cobalt complex is used as a starting material for preparing the 2-(cyclohexenylidene) malonic acid derivative (*Organometallics* 1989, 8(10), 2474). The cyclohexadiene cobalt complex reacts with dimethyl malonate at −78° C. in the presence of a strong base LDA to produce dimethyl 2-(cyclohexenylidene) malonate. This reaction can afford the target product in moderate yield; however, large amount of metallic reagents and ultra-low temperature operation are required, causing high cost, high pollution of this method, making it not suitable for industrial production.

Because of the scarcity of efficient method for the synthesis of 2-(cyclohexenylidene) malonic acid derivative with multiple functional groups, the applications of this class of compound in organic synthesis especially in pharmaceutical preparation are extremely limited.

The first object of the present invention is to provide an efficient method for synthesizing 2-(cyclohexenylidene) malonic acid derivatives, particularly the sterically more hindered 2-(2,6-disubstituted cyclohexenylidene) malonic acid derivatives.

The second object of the present invention is to provide a use of 2-(cyclohexenylidene) malonic acid derivatives, particularly the sterically more hindered 2-(2,6-disubstituted cyclohexenylidene) malonic acid derivative, in the organic synthesis.

The inventors of the present invention, through numerous research and exploration, have successfully developed a method for preparing 2-(cyclohexenylidene) malonic acid derivatives, particularly 2-(2,6-disubstituted cyclohexenylidene) malonic acid derivatives. Meanwhile, the inventors of the present invention, through further research, have successfully applied this method and the intermediates to the synthesis of 2-aryl malonic acid derivatives and their corresponding drugs such as Pinoxaden (CAS 243973-20-8).

SUMMARY

The first object of the present invention is to provide a new method for synthesizing 2-(cyclohexenylidene) malonic acid derivatives in which an olefin (1) is used as starting material. This method comprises the step of: cyclizing compound (1) with compound (2) in the presence of catalyst A to give the 2-(cyclohexenylidene) malonic acid derivative (4) via intermediate (3), as shown in the following reaction scheme:

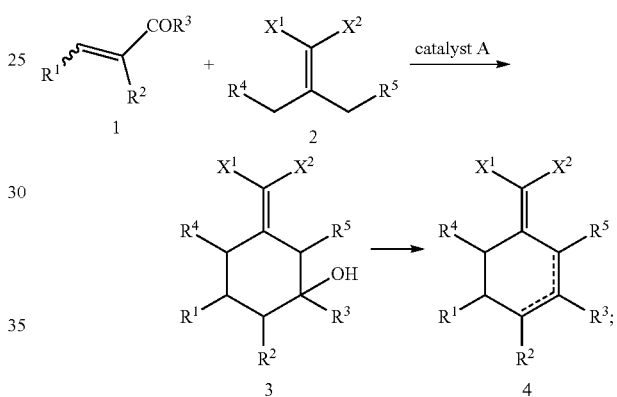

wherein:

$R^1$, $R^2$, $R^3$, $R^4$ and $R^5$ each are independently hydrogen, a $C_1$-$C_{10}$ alkyl group, a $C_6$-$C_{12}$ aryl group or a heteroaryl group containing one or two atoms selected from nitrogen, oxygen and sulfur; and $X^1$ and $X^2$ each are independently a cyano group or —$COR^6$ where $R^6$ is selected from hydrogen, a $C_1$-$C_{10}$ alkyl group, a $C_1$-$C_{10}$ alkoxy group, a $C_6$-$C_{12}$ aryloxy group, a $C_1$-$C_{10}$ alkylamino group, a $C_6$-$C_{12}$ arylamino group, a di($C_1$-$C_{10}$ alkyl) amino group, a ($C_1$-$C_{10}$ alkyl)($C_6$-$C_{12}$ aryl) amino group, a di($C_6$-$C_{12}$ aryl) amino group, a $C_6$-$C_{12}$ aryl group or a heteroaryl group containing one or two atoms selected from nitrogen, oxygen and sulfur.

The inventors of the present invention have also found that compound (1) and compound (2) may undergo cyclization reaction in the presence of the catalyst A, to produce the 2-(cyclohexenylidene) malonic acid derivative (4) directly in a "one-pot" method without separation of the intermediate (3), as shown in the following reaction scheme:

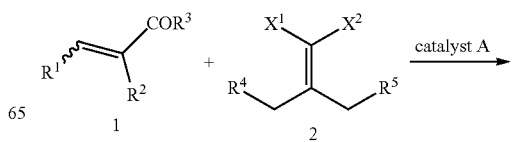

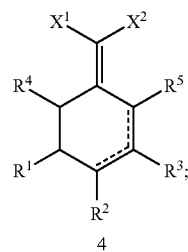

wherein:

R[1], R[2], R[3], R[4] and R[5] each are independently hydrogen, a $C_1$-$C_{10}$ alkyl group, a $C_6$-$C_{12}$ aryl group or a heteroaryl group containing one or two atoms selected from nitrogen, oxygen and sulfur; and X[1] and X[2] each are independently a cyano group or —COR[6] where R[6] is selected from hydrogen, a $C_1$-$C_{10}$ alkyl group, a $C_1$-$C_{10}$ alkoxy group, a $C_6$-$C_{12}$ aryloxy group, a $C_1$-$C_{10}$ alkylamino group, a $C_6$-$C_{12}$ arylamino group, a di($C_1$-$C_{10}$ alkyl) amino group, a ($C_1$-$C_{10}$ alkyl)($C_6$-$C_{12}$ aryl) amino group, a di($C_6$-$C_{12}$ aryl) amino group, a $C_6$-$C_{12}$ aryl group or a heteroaryl group containing one or two atoms selected from nitrogen, oxygen and sulfur.

A molar ratio of compound (1) to compound (2) is 0.8-2.0:1, preferably, 1.0-1.5:1.

The catalyst A used for the cyclization reaction may be an organic acid, including but not limited to acetic acid, propionic acid and TsOH; an organic base, including but not limited to Et₃N, DABCO, TBU, pyrrolidine and piperidine; an inorganic base, including but not limited to potassium carbonate, sodium carbonate, potassium hydroxide, sodium methoxide and sodium hydride; or a mixture thereof; preferably, Et₃N and DABCO.

A molar ratio of the catalyst A to compound (2) is 0.005-2.4:1, preferably 0.1-1.0:1.

A solvent for the cyclization reaction is selected from water, an organic solvent, or a mixture thereof. The organic solvent may be an aromatic hydrocarbon such as benzene, toluene and chlorobenzene, an alcohol such as methanol and ethanol, an ether such as diethyl ether and tetrahydrofuran, a nitrile such as acetonitrile, an ester such as ethyl acetate, an amide such as N,N-dimethylformamide, or a sulfone/sulfoxide such as dimethyl sulfoxide; preferably, toluene.

The cyclization reaction may be carried out in the absence of a solvent.

A temperature of the cyclization reaction is 0-150° C., preferably 80-130° C.

The second object of the present invention is to provide a method for preparing 2-aryl malonic acid derivatives from the 2-(cyclohexenylidene) malonic acid derivatives, comprising: aromatizing compound (4) in the presence of catalyst B to give a 2-aryl malonic acid derivative (5), as shown in the following reaction scheme:

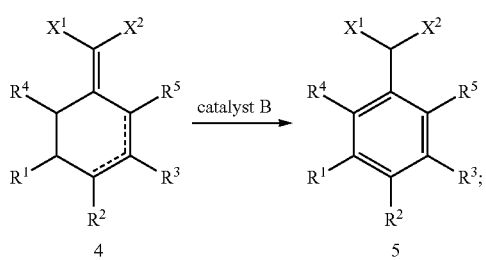

wherein:

R[1], R[2], R[3], R[4] and R[5] each are independently hydrogen, a $C_1$-$C_{10}$ alkyl group, a $C_6$-$C_{12}$ aryl group or a heteroaryl group containing one or two atoms selected from nitrogen, oxygen and sulfur; and X[1] and X[2] each are independently a cyano group or —COR[6] where R[6] is selected from hydrogen, a $C_1$-$C_{10}$ alkyl group, a $C_1$-$C_{10}$ alkoxy group, a $C_6$-$C_{12}$ aryloxy group, a $C_1$-$C_{10}$ alkylamino group, a $C_6$-$C_{12}$ arylamino group, a di($C_1$-$C_{10}$ alkyl) amino group, a ($C_1$-$C_{10}$ alkyl)($C_6$-$C_{12}$ aryl) amino group, a di($C_6$-$C_{12}$ aryl) amino group, a $C_6$-$C_{12}$ aryl group or a heteroaryl group containing one or two atoms selected from nitrogen, oxygen and sulfur.

The catalyst B is a metal catalyst, preferably Pd/C. A temperature of the aromatization reaction is 100-400° C., preferably 180-220° C. The aromatization reaction is carried out in the absence of a solvent or in the presence of a solvent selected from an alcohol, an ether, an ester, an amide or an aromatic hydrocarbon having a boiling point higher than 150° C.

The present invention provides a new method for preparing the 2-(cyclohexenylidene) malonic acid derivative and uses thereof. This method employs a completely different synthetic strategy from the technologies known in the prior arts, where the technologies known in the prior art all use raw materials with cyclohexane skeleton to produce the 2-(cyclohexenylidene) malonic acid derivatives; whereas, the present invention uses non-cyclohexane skeleton-based raw materials for the preparation of the 2-(cyclohexenylidene) malonic acid derivatives. Furthermore, this method has particularly the following advantages: (1) the method can be very efficiently used for the synthesis of highly sterically-hindered target products, such as 2-(2,6-disubstituted cyclohexenylidene) malonic acid derivatives; (2) the reaction yield is high, the reaction conditions are mild, and the wastes are less, favorable for industrial production. More importantly, the present invention extends the further use of 2-(cyclohexenylidene) malonic acid derivatives in organic synthesis, especially in the synthesis of 2-aryl malonic acid derivatives and their corresponding drugs such as Pinoxaden.

DETAILED DESCRIPTION OF EMBODIMENTS

Some features of the invention will be further illustrated with reference to the following embodiments, but the embodiments are not intended to limit the scope of the invention.

Starting material olefin 1 can be readily purchased commercially or prepared from aldehydes and ketones by methods well known in the prior art (for example, *J. Am. Chem. Soc.* 136 (28), 2014, 9918-9921; *Tetrahedron*, 70 (13), 2014, 2257-2263). The raw material 2 can be easily prepared from ketones and malonic acid derivatives by methods well known in the prior art (for example, *Eur. Med. Chem.* 85, 2014, 450-457; WO 2011098398).

Preparation of 2-(4-heptylidene) malononitrile

To a reaction flask were sequentially added 65.0 g of 4-heptanone (0.569 mol), 39.4 g of malononitrile (0.569 mol), 6.6 g of ammonium acetate (0.086 mol), 10.3 g of acetic acid (0.171 mol) and toluene. The reaction mixture was refluxed, and the resulted water was removed. After the reaction was complete, the reaction mixture was cooled, washed with water, concentrated and purified to give 84.9 g of 2-(4-heptylidene) malononitrile, and the yield was 92%.

$^1$H NMR (CDCl$_3$, 500 MHz, TMS): δ 2.57-2.53 (m, 4H), 1.64-1.60 (m, 4H), 1.02 (t, J=7.5 Hz, 6H).
$^{13}$C NMR (CDCl$_3$, 125 MHz): δ 186.08, 111.88, 85.91, 37.47, 21.44, 12.81.

Preparation of
2-(1-(4-methoxyphenyl)-2-propylidene)
malononitrile

To a reaction flask were sequentially added 82.1 g of 1-(4-methoxyphenyl)-2-propanone (0.50 mol), 33.0 g of malononitrile (0.50 mol), 5.8 g of ammonium acetate (0.075 mol), 9.0 g of acetic acid (0.15 mol) and toluene. The reaction mixture was refluxed, and the resulted water was removed. After the reaction was complete, the reaction mixture was cooled, washed with water, concentrated and purified to give 100.8 g of 2-(1-(4-methoxyphenyl)-2-propylidene) malononitrile, and the yield was 95%.
$^1$H NMR (CDCl$_3$, 500 MHz, TMS): δ 7.12 (d, J=11 Hz, 2H), 6.88 (d, J=11 Hz, 2H), 3.80 (s, 5H), 2.17 (s, 3H).
$^{13}$C NMR (CDCl$_3$, 125 MHz): δ 180.2, 159.2, 129.9, 126.1, 114.5, 112.0, 111.7, 85.6, 55.2, 42.6, 22.0.

Example 1 Preparation of
2-(2,6-diethyl-4-methyl-2-ene-1-cyclohexylidene)
malononitrile 24.3 g of 2-(4-Heptylidene) malononitrile (0.15 mol), 10.5 g of 2-methylpropenal (0.15 mol) and 15.2 g of triethylamine (0.15 mol) were sequentially added to toluene.
The reaction mixture was refluxed until the reaction was complete. Then, the reaction mixture was cooled, washed with 1 N diluted hydrochloric acid, dried, concentrated and purified to give 25.7 g of 2-(2,6-diethyl-4-methyl-2-ene-1-cyclohexylidene) malononitrile, and the yield was 80%.
$^1$H NMR (CDCl$_3$, 500 MHz, TMS): δ6.14-6.14 (m, 1H), 3.08-3.04 (m, 1H), 2.82-2.75 (m, 1H), 2.57-2.46 (m, 2H), 2.04-2.01 (m, 1H), 1.56-1.51 (m, 2H), 1.48-1.41 (m, 1H), 1.12-1.01 (m, 6H), 1.00-0.98 (m, 3H).
$^{13}$C NMR (CDCl$_3$, 125 MHz): δ 175.12, 148.74, 134.78, 113.99, 113.74, 43.75, 34.75, 28.13, 16.55, 15.52, 20.91, 13.59, 11.98.

Example 2 Preparation of Mixture of 2-(2,6-diethyl-4-methyl-2-ene-1-cyclohexylidene) malononitrile and 2-(2,6-diethyl-4-methyl-3-ene-1-cyclohexylidene) malononitrile 25.0 g of 2-(4-Heptylidene) malononitrile (0.154 mol), 14.0 g of 2-methylpropenal (0.200 mol) and 15.6 g of triethylamine (0.154 mol) were sequentially added to toluene. The reaction mixture was refluxed until the reaction was complete. Then, the reaction mixture was cooled, washed with 1 N diluted hydrochloric acid, dried and concentrated to give 30.4 g of the mixture of 2-(2,6-diethyl-4-methyl-2-ene-1-cyclohexylidene) malononitrile and 2-(2,6-diethyl-4-methyl-3-ene-1-cyclohexylidene) malononitrile in a ratio of 91:9 by GC-MS analysis.

Example 3 Preparation of 2-(2,6-diethyl-3-hydroxy-4-methyl-1-cyclohexyliene) malononitrile 3.2 g of 2-(4-Heptylidene) malononitrile (0.02 mol), 1.4 g of 2-methylpropenal (0.02 mol) and 2.0 g of triethylamine (0.02 mol) were sequentially added to toluene to react at 50° C. for 5 h. Then the reaction mixture was cooled, washed with 1 N diluted hydrochloric acid, dried, concentrated and purified to give 4.4 g of 2-(2,6-diethyl-3-hydroxy-4-methyl-1-cyclohexyliene) malononitrile, and the yield was 95% yield.
$^1$H NMR (CDCl$_3$, 500 MHz, TMS): δ 3.82 (s, 1H), 3.11-3.08 (m, 1H), 3.03-2.99 (m, 1H), 2.06-2.05 (m, 1H), 1.87-1.81 (m, 2H), 1.73-1.65 (m, 2H), 1.62-1.52 (m, 3H), 1.08-1.02 (m, 9H).
$^{13}$C NMR (CDCl$_3$, 125 MHz): δ 188.8, 112.2, 112.0, 87.1, 75.1, 53.1, 44.0, 30.9, 28.4, 26.4, 26.0, 17.4, 12.9.

Example 4 Preparation of
2-(2,6-diethyl-4-methyl-2-ene-1-cyclohexylidene)
malononitrile 2.3 g of 2-(2,6-Diethyl-3-hydroxy-4-methyl-1-cyclohexyliene) malononitrile (0.01 mol) prepared in Example 3 and a solution of 1.0 g of triethylamine (0.01 mol) in toluene were reacted under reflux. After the reaction was complete, the reaction mixture was cooled, washed with 1 N diluted hydrochloric acid, dried, concentrated and purified to give 1.8 g of 2-(2,6-diethyl-4-methyl-2-ene-1-cyclohexylidene) malononitrile, and the yield was 84%.

Example 5 Preparation of
2-(2,6-diethyl-4-methyl-2-ene-1-cyclohexylidene)
malononitrile 32.4 g of 2-(4-Heptylidene) malononitrile (0.20 mol), 14.0 g of 2-methylpropenal (0.20 mol) and 2.2 g of triethylenediamine (0.02 mol) were sequentially added to toluene to react at 130° C. After the reaction was complete, the reaction mixture was cooled, washed with 1 N diluted hydrochloric acid, extracted with ethyl acetate, dried, concentrated and purified to give 39.4 g of 2-(2,6-diethyl-4-methyl-2-ene-1-cyclohexylidene) malononitrile, and the yield was 92%.

Example 6 Preparation of
2-(2,6-diethyl-4-methyl-2-ene-1-cyclohexylidene)
malononitrile A solution of 48.7 g of 2-(4-heptylidene) malononitrile (0.30 mol) in THF was dropwise added to a solution of 12.4 g of NaH (0.31 mol) in THF at 0-5° C. After addition, the mixture was warmed to room temperature and then reacted for 20 min. Then a solution of 27.3 g of 2-methylpropenal (0.39 mol) in THF was dropwise added. The reaction mixture was heated and then refluxed until the reaction was complete. The reaction mixture was cooled, quenched with 1 N diluted hydrochloric acid, extracted with ethyl acetate, dried, concentrated and purified to give 13.5 g of 2-(2,6-diethyl-4-methyl-2-ene-1-cyclohexylidene) malononitrile.

Example 7 Preparation of
2-(2,6-diethyl-4-methyl-2-ene-1-cyclohexylidene)
malononitrile To a reaction flask were sequentially added 25.0 g of 2-(4-heptylidene) malononitrile (0.154 mol), 14.0 of 2-methylpropenal (0.20 mol) and 3.4 g of triethylenediamine (0.031 mol). The reaction mixture was reacted at 80° C. After the reaction was complete, the reaction mixture was cooled, dissolved in ethyl acetate, washed with 1 N diluted hydrochloric acid, dried and concentrated by distillation to give 21.4 g of the target product.

Example 8 Preparation of Mixture of 2-(2,6-diethyl-5-phenyl-2-ene-1-cyclohexylidene) malononitrile and 2-(2,6-diethyl-5-phenyl-3-ene-1-cyclohexylidene) malononitrile 64.9 g of 2-(4-Heptylidene) malononitrile (0.40 mol), 68.7 g of cinnamaldehyde (0.52 mol) and 40.5 g of triethylamine (0.40 mol) were sequentially added to toluene. The reaction mixture was refluxed until the reaction was complete. Then, the reaction mixture was cooled, washed with 1 N diluted hydrochloric acid, dried and concentrated to give 83.4 g of the mixture of 2-(2,6-diethyl-5-phenyl-2-ene-1-cyclohexylidene) malononitrile and 2-(2,6-diethyl-5-phenyl-3-ene-1-cyclohexylidene) malononitrile in a ratio of 94:6 by GC-MS analysis. The resulting mixture was further purified to give 77.4 g of 2-(2,6-diethyl-5-phenyl-2-ene-1-cyclohexylidene) malononitrile, and the yield was 70%.

$^1$H NMR (CDCl$_3$, 500 MHz, TMS): δ 7.31-7.28 (m, 2H), 7.26-7.23 (m, 1H), 7.08-7.06 (m, 2H), 6.36-6.25 (m, 1H), 3.31 (d, 1H, J=5.0 Hz), 3.21-3.18 (m, 1H), 2.86-2.77 (m, 2H), 2.67 (dd, 1H, J$_1$=20.5 Hz, J$_2$=4.0 Hz), 2.59-2.51 (m, 1H), 1.77-1.70 (m, 1H), 1.65-1.59 (m, 1H), 1.12 (t, 3H, J=7.5 Hz), 1.05 (t, 3H, J=7.5 Hz).

$^{13}$C NMR (CDCl$_3$, 125 MHz): δ 173.0, 142.4, 139.7, 136.7, 128.7, 127.0, 126.5, 113.3, 81.0, 51.5, 41.7, 28.0, 27.6, 26.7, 13.5, 12.1.

Example 9 Preparation of 2-(6-(4-methoxyphenyl)-4-methyl-2-ene-1-cyclohexylidene) malononitrile 31.8 g of 2-(1-(4-Methoxyphenyl)-2-propylidene) malononitrile (0.15 mol), 14.0 g of 2-methylpropenal (0.20 mol) and 15.2 g of triethylamine (0.15 mol) were sequentially added to toluene. The reaction mixture was refluxed until the reaction was complete. Then, the reaction mixture was cooled, washed with 1 N diluted hydrochloric acid, dried, concentrated and purified to give 34.9 g of 2-(6-(4-methoxyphenyl)-4-methyl-2-ene-1-cyclohexylidene) malononitrile, and the yield was 93%.

$^1$H NMR (CDCl$_3$, 500 MHz, TMS): δ 9.02-7.00 (m, 2H), 6.94 (dd, J$_1$=10.0 Hz, J$_2$=2.5 Hz, 1H), 6.85-6.84 (m, 2H), 6.67 (d, J=10.0 Hz, 1H), 4.27-4.25 (m, 1H), 3.78 (s, 3H), 2.39-2.31 (m, 1H), 2.08-2.04 (m, 1H), 1.76-1.71 (m, 1H), 1.10 (d, J=7.5 Hz, 3H).

$^{13}$C NMR (CDCl$_3$, 125 MHz): δ 170.7, 158.8, 155.3, 130.4, 130.3, 128.1, 124.5, 114.3, 114.1, 112.2, 111.9, 82.1, 55.2, 43.4, 37.7, 27.5, 19.9.

Example 10 Preparation of 2-(2,6-diphenyl-4-methyl-2-ene-1-cyclohexylidene) malononitrile 77.5 g of 2-(2,6-Diphenylpropylidene) malononitrile (0.30 mol), 23.1 g of 2-methylpropenal (0.33 mol) and 30.3 g of triethylamine (0.30 mol) were sequentially added to toluene. The reaction mixture was refluxed until the reaction was complete. Then, the reaction mixture was cooled, washed with 1 N diluted hydrochloric acid, dried, concentrated and purified to give 91.2 g of 2-(2,6-diphenyl-4-methyl-2-ene-1-cyclohexylidene) malononitrile, and the yield was 98%.

$^1$H NMR (CDCl$_3$, 500 MHz, TMS): δ 7.46-7.24 (m, 1H), 6.38-6.37 (m, 1H), 4.54-4.52 (m, 1H), 2.57-2.51 (m, 1H), 2.36-2.30 (m, 1H), 1.95-1.88 (m, 1H), 1.17 (d, J=9.0 Hz, 3H).

$^{13}$C NMR (CDCl$_3$, 125 MHz): δ 169.9, 153.1, 138.4, 137.8, 137.4, 129.1, 129.0, 128.8, 127.6, 127.0, 113.6, 110.9, 83.9, 45.9, 37.2, 28.5, 20.4.

Example 11 Preparation of 2-(3-methyl-2-ene-1-cyclohexylidene) malononitrile 26.5 g of 2-(2-Propylidene) malononitrile (0.25 mol), 22.8 g of vinyl methyl ketone (0.32 mol) and 25.2 g of triethylamine (0.25 mol) were sequentially added to toluene. The reaction mixture was refluxed until the reaction was complete. Then, the reaction mixture was cooled, washed with 1 N diluted hydrochloric acid, dried, concentrated and purified to give 26.1 g of 2-(3-methyl-2-ene-1-cyclohexylidene) malononitrile.

$^1$H NMR (CDCl$_3$, 500 MHz, TMS): δ6.61-6.61 (m, 1H), 2.72 (t, J=6.5 Hz, 2H), 2.34 (t, J=7.5 Hz, 2H), 2.07-2.07 (m, 3H), 1.91-1.85 (m, 2H).

$^{13}$C NMR (CDCl$_3$, 125 MHz): δ 170.7, 162.1, 121.5, 113.0, 112.3, 31.1, 28.9, 25.2, 21.2.

Example 12 Preparation of methyl 2-cyano-2-(2,6-diethyl-4-methyl-1-cyclohexenylidene) acetate 58.6 g of Methyl 2-cyano-3-propyl-2-hexenoate (0.300 mol), 27.3 g of 2-methylpropenal (0.390 mol) and 30.3 g of triethylamine (0.300 mol) were sequentially added to toluene. The reaction mixture was refluxed until the reaction was complete. Then, the reaction mixture was cooled, washed with 1 N diluted hydrochloric acid, dried and concentrated to give 62.8 g of methyl 2-cyano-2-(2,6-diethyl-4-methyl-1-cyclohexenylidene) acetate, and the yield was 84%.

$^1$H NMR (CDCl$_3$, 500 MHz, TMS): δ 6.02-5.90 (m, 1H), 3.83-3.82 (m, 3H), 3.63-3.07 (m, 1H), 2.91-2.44 (m, 2H), 2.22-1.95 (m, 2H), 1.58-1.42 (m, 3H), 1.08-1.04 (m, 4H), 1.00-0.90 (m, 5H).

Example 13 Preparation of diethyl 2-(3-methyl-2-ene-1-cyclohexylidene) malonate 120.1 g of Diethyl 2-(2-propylidene) malonate (0.60 mol), 54.7 g of vinyl methyl ketone (0.78 mol) and 60.6 g of triethylamine (0.60 mol) were sequentially added to toluene. The reaction mixture was refluxed until the reaction was complete. Then, the reaction mixture was cooled, washed with 1N diluted hydrochloric acid, dried and concentrated by distillation to give 60.5 g of diethyl 2-(3-methyl-2-ene-1-cyclohexylidene) malonate.

$^1$H NMR (CDCl$_3$, 500 MHz, TMS): δ6.61-6.60 (m, 1H), 4.28-4.18 (m, 4H), 2.65 (t, J=8.0 Hz, 2H), 2.15 (t, J=8.0 Hz, 2H), 1.898 (d, J=1.5 Hz, 1H), 1.80-1.73 (m, 2H), 1.32-1.26 (m, 6H).

$^{13}$C NMR (CDCl$_3$, 125 MHz): δ 165.8, 165.8, 151.9, 151.6, 121.4, 118.7, 60.6, 60.4, 30.6, 27.1, 24.8, 21.8, 13.9.

Example 14 Preparation of 2-(2,6-diethyl-4-methylphenyl) malononitrile 214.1 g of 2-(2,6-Diethyl-4-methyl-2-ene-1-cyclohexylidene) malononitrile (1 mol) and 2.2 g of Pd/C were heated to 180° C. under a nitrogen atmosphere. After the reaction was complete, the reaction mixture was cooled, and ethyl acetate was added. The mixture was filtered to remove the catalyst (Pd/C). A small amount of solvent was used to wash the catalyst. The organic phase was dried and crystallized by concentration to give 188.9 g of 2-(2,6-diethyl-4-methylphenyl) malononitrile, and the yield was 89%.

Example 15 Preparation of 2-(2,6-diphenyl-4-methylphenyl) malononitrile 15.5 g of 2-(2,6-Diphenyl-4-methyl-2-ene-1-cyclohexylidene) malononitrile (0.05 mol) and 0.8 g of Pd/C was heated to 220° C. After the reaction was complete, the reaction mixture was cooled and filtered to remove the catalyst (Pd/C). A small amount of solvent was used to wash the catalyst. The organic phase was concentrated to give 10.9 g of 2-(2,6-diphenyl-4-methylphenyl) malononitrile, and the yield was 71%.

$^1$H NMR (CDCl$_3$, 500 MHz, TMS): δ 7.54-7.46 (m, 10H), 7.21 (s, 2H), 5.11 (s, 1H), 2.44 (s, 3H).

$^{13}$C NMR (CDCl$_3$, 125 MHz): δ 143.4, 140.2, 138.8, 131.6, 129.4, 129.0, 128.7, 119.7, 112.2, 24.4, 21.0.

Example 16 Preparation of diethyl 2-(3-methylphenyl)malonate 20.0 g of Diethyl 2-(3-methyl-2-ene-1-cyclohexylidene) malonate (0.08 mol) and 0.04 g of Pt/C were heated to 160° C. in N,N-dimethylacetamide. After the reaction was complete, the reaction mixture was cooled and filtered to remove the catalyst (Pt/C). A small amount of solvent was used to wash the catalyst. The organic phase was concentrated to give 16.6 g of diethyl 2-(3-methylphenyl) malonate, and the yield was 84%.

$^1$H NMR (CDCl$_3$, 500 MHz, TMS): δ 7.27-7.13 (m, 4H), 4.57 (s, 1H), 4.20 (q, J=7.0 Hz, 4H), 2.35 (s, 3H), 1.26 (t, J=7.0 Hz, 6H).

$^{13}$C NMR (CDCl$_3$, 125 MHz): δ 168.2, 138.2, 132.6, 129.8, 128.9, 128.4, 126.2, 61.7, 57.8, 14.0, 13.9.

Example 17 Preparation of dimethyl 2-(2,6-diethyl-4-methyl-2-ene-1-cyclohexylidene) malonate To a reaction flask were sequentially added with 22.8 g of dimethyl 2-(4-heptylidene) malonate (0.10 mol), 7.0 g of 2-methylpropenal (0.10 mol) and 2.2 g of triethylenediamine (0.02 mol) to react by heating. After the reaction was complete, the reaction mixture was cooled, dissolved with ethyl acetate, washed with 1N diluted hydrochloric acid, dried and concentrated to give dimethyl 2-(2,6-diethyl-4-methyl-2-ene-1-cyclohexylidene) malonate.

Example 18 Preparation of dimethyl 2-(2,6-diethyl-4-methylphenyl) malonate

Dimethyl 2-(2,6-diethyl-4-methyl-2-ene-1-cyclohexylidene) malonate prepared in Example 17 and 1.1 g of Pd/C were heated to 180° C. under a nitrogen atmosphere. After the reaction was complete, the reaction mixture was cooled, and ethyl acetate was added. The mixture was filtered to remove the solid. The organic phase was dried and concentrated to give 22.2 g of dimethyl 2-(2,6-diethyl-4-methylphenyl) malonate, and the yield was 80%.

$^1$H NMR (CDCl$_3$, 500 MHz, TMS): δ 6.93 (s, 2H), 5.06 (s, 1H), 3.73 (s, 6H), 2.64 (q, J=7.0 Hz, 4H), 2.30 (s, 3H), 1.18 (t, J=7.0 Hz, 6H).

$^{13}$C NMR (CDCl$_3$, 125 MHz): δ 15.2, 21.1, 26.6, 51.5, 52.6, 126.4, 127.9, 137.9, 143.6, 169.3.

Example 19 Preparation of Pinoxaden 15.3 g of Dimethyl 2-(2,6-diethyl-4-methylphenyl) malonate prepared in Example 18 (0.05 mol), 10.5 g of hexahydro-1,4,5-oxadiazepine dihydrochloride (0.06 mol) and 20.2 g of triethylamine (0.20 mol) were stirred to react in xylene under refluxing temperature. After the reaction was complete, the reaction mixture was cooled. 10.8 g of Pivaloyl chloride (0.09 mol) was added. The mixture was reacted at room temperature. After the reaction was complete, the reaction mixture was adjusted to be acidic with dilute hydrochloric acid and then extracted with ethyl acetate. The organic phases were combined, dried and crystallized by concentration to give 14.4 g of Pinoxaden, and the yield was 72%.

$^1$H NMR (CDCl$_3$, 500 MHz, TMS): δ8.88 (s, 2H), 4.28-4.26 (m, 2H), 3.94-3.93 (m, 2H), 3.89-3.83 (m, 4H), 2.56-2.47 (m, 2H), 2.45-2.40 (m, 2H), 2.39 (s, 3H), 1.12 (t, J=9.0 Hz, 3H), 1.23 (s, 9H).

What is claimed is:

1. A method for preparing 2-(cyclohexenylidene) malonic acid derivatives, comprising: cyclizing compound (1) with compound (2) in the presence of a catalyst A to produce compound (4) via intermediate (3); or cyclizing compound (1) with compound (2) in the presence of a catalyst A to produce compound (4) directly, as shown in the following reaction scheme:

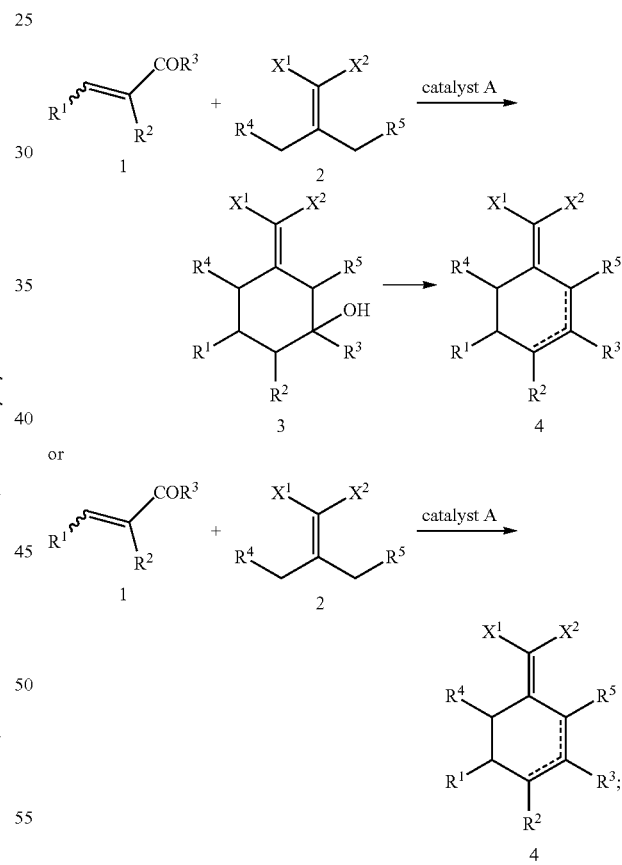

wherein:

$R^1$, $R^2$, $R^3$, $R^4$ and $R^5$ each are independently hydrogen, a $C_1$-$C_{10}$ alkyl group, a $C_6$-$C_{12}$ aryl group or a heteroaryl group containing one or two atoms selected from nitrogen, oxygen and sulfur; and $X^1$ and $X^2$ each are independently a cyano group or —COR$^6$ where R$^6$ is selected from hydrogen, a $C_1$-$C_{10}$ alkyl group, a $C_1$-$C_{10}$ alkoxy group, a $C_6$-$C_{12}$ aryloxy group, a $C_1$-$C_{10}$ alkylamino group, a $C_6$-$C_{12}$ arylamino group, a di($C_1$-$C_{10}$ alkyl) amino group, a ($C_1$-$C_{10}$ alkyl)($C_6$-$C_{12}$ aryl) amino group, a di($C_6$-$C_{12}$ aryl) amino group, a $C_6$-$C_{12}$ aryl group or a heteroaryl group containing one or two atoms selected from nitrogen, oxygen and sulfur;

wherein the catalyst A is selected from the group consisting of an organic acid, an organic base, an inorganic base and a mixture thereof.

2. The method of claim 1, wherein a molar ratio of compound (1) to compound (2) is 0.8-2.0:1; a molar ratio of catalyst A to compound (2) is 0.005-2.4:1; a cyclization reaction temperature is 0-150° C.; and the cyclization reaction is carried out in the absence of a solvent or in the presence of a solvent selected from water, an organic solvent or a mixture thereof.

3. The method of claim 2, wherein the molar ratio of compound (1) to compound (2) is 1.0-1.5:1; the catalyst A used for the cyclization reaction is $Et_3N$ and DABCO; the molar ratio of catalyst A to compound (2) is 0.1-1.0:1; the cyclization reaction temperature is 80-130° C.; and the solvent for the cyclization reaction is toluene.

4. A compound of formula (3) or (4) or a mixture thereof,

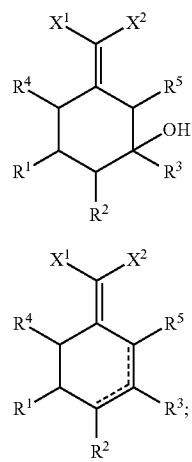

wherein:
$R^4$ is selected from a $C_1$-$C_{10}$ alkyl group, a $C_6$-$C_{12}$ aryl group or a heteroaryl group containing one or two atoms selected from nitrogen, oxygen and sulfur; $R^1$, $R^2$, $R^3$ and $R^5$ each are independently hydrogen, a $C_1$-$C_{10}$ alkyl group, a $C_6$-$C_{12}$ aryl group or a heteroaryl group containing one or two atoms selected from nitrogen, oxygen and sulfur; and $X^1$ and $X^2$ each are independently a cyano group or —$COR^6$ where $R^6$ is selected from hydrogen, a $C_1$-$C_{10}$ alkyl group, a $C_1$-$C_{10}$ alkoxy group, a $C_6$-$C_{12}$ aryloxy group, a $C_1$-$C_{10}$ alkylamino group, a $C_6$-$C_{12}$ arylamino group, a di($C_1$-$C_{10}$ alkyl) amino group, a ($C_1$-$C_{10}$ alkyl)($C_6$-$C_{12}$ aryl) amino group, a di($C_6$-$C_{12}$ aryl) amino group, a $C_6$-$C_{12}$ aryl group or a heteroaryl group containing one or two atoms selected from nitrogen, oxygen and sulfur.

5. The compound of claim 4, wherein $R^4$ is a $C_1$-$C_4$ alkyl group or a $C_6$-$C_{12}$ aryl group; $R^1$, $R^2$, $R^3$ and $R^5$ each are independently hydrogen, a $C_1$-$C_4$ alkyl group or a $C_6$-$C_{12}$ aryl group; $X^1$ and $X^2$ each are independently a cyano group, —COOMe or COOEt.

6. A method for preparing a 2-aryl malonic acid derivative, comprising:
1) cyclizing compound (1) with compound (2) in the presence of a catalyst A to produce compound (4) via intermediate (3); or cyclizing compound (1) with compound (2) in the presence of a catalyst A to produce compound (4) directly, as shown in the following reaction scheme:

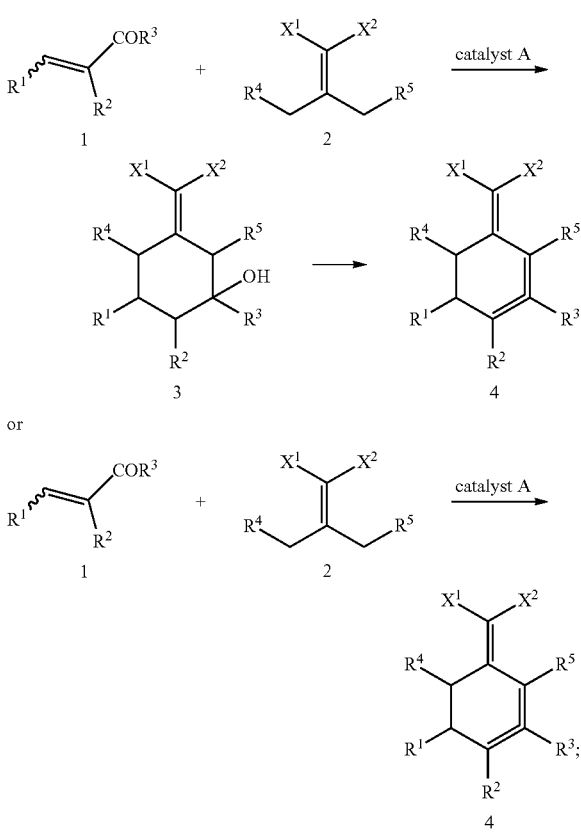

and
2) aromatizing compound (4) in the presence of a catalyst B to give the 2-aryl malonic acid derivative (5), as shown in the following reaction scheme:

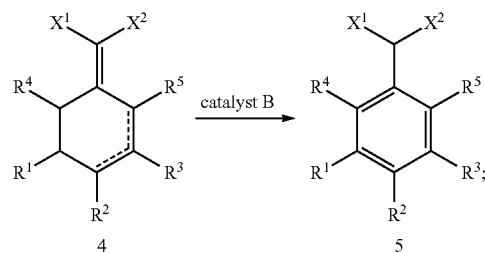

wherein:
$R^1$, $R^2$, $R^3$, $R^4$ and $R^5$ each are independently hydrogen, a $C_1$-$C_{10}$ alkyl group, a $C_6$-$C_{12}$ aryl group or a heteroaryl group containing one or two atoms selected from nitrogen, oxygen or sulfur; and
$X^1$ and $X^2$ each are independently a cyano group or —$COR^6$ where $R^6$ is selected from hydrogen, a $C_1$-$C_{10}$ alkyl group, a $C_1$-$C_{10}$ alkoxy group, a $C_6$-$C_{12}$ aryloxy group, a $C_1$-$C_{10}$ alkylamino group, a $C_6$-$C_{12}$ arylamino group, a di($C_1$-$C_{10}$ alkyl) amino group, a ($C_1$-$C_{10}$ alkyl)($C_6$-$C_{12}$ aryl) amino group, a di($C_6$-$C_{12}$ aryl) amino group, a $C_6$-$C_{12}$ arylgroup or a heteroaryl group containing one or two atoms selected from nitrogen, oxygen and sulfur;

wherein the catalyst A is selected from the group consisting of an organic acid, an organic base, an inorganic base and a mixture thereof; and the catalyst B is a metal catalyst.

7. The method of claim 6, wherein an aromatization reaction temperature is 100-400° C.; and the aromatization reaction is carried out in the absence of a solvent or in the presence of a solvent selected from an alcohol, an ether, an ester, an amide or an aromatic hydrocarbon having a boiling point higher than 150° C.

8. The method of claim 7, wherein the catalyst B is Pd/C; and the aromatization temperature is 180-220° C.

9. A method for synthesizing Pinoxaden, comprising:
1) cyclizing methacrylaldehyde (1) with 2-(heptan-4-ylidene)malonate (2) to produce 2-(2,6-diethyl-4-methylcyclohex-2-en-1-ylidene)malonate (4) via 2-(2,6-diethyl-3-hydroxy-4-methyl-cyclohexylidene)malonate (3) in the presence of a catalyst A; or cyclizing methacrylaldehyde (1) with 2-(heptan-4-ylidene)malonate (2) in the presence of a catalyst A to produce 2-(2,6-diethyl-4-methylcyclohex-2-en-1-ylidene)malonate (4) directly;
2) aromatizing 2-(2,6-diethyl-4-methylcyclohex-2-en-1-ylidene)malonate (4) in the presence of a catalyst B to give a 2-(2,6-diethyl-4-methylphenyl)malonate (5); and
3) reacting 2-(2,6-diethyl-4-methylphenyl)malonate (5) with hexahydro-1,4,5-oxadiazapine (6) to produce compound (7); and then adding pivaloyl chloride to the reaction to obtain Pinoxaden, as shown in the following reaction scheme:

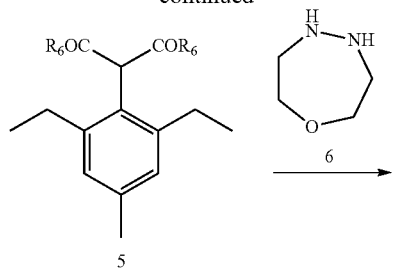

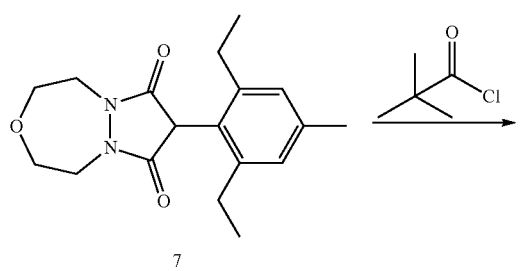

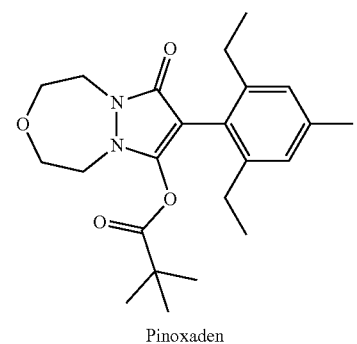

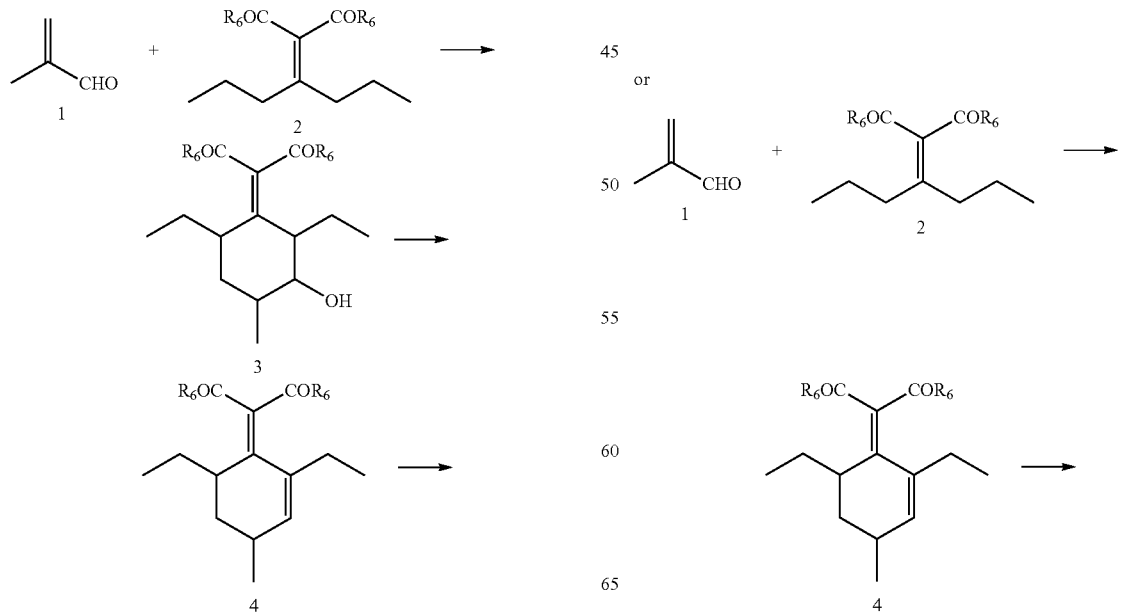

15
-continued

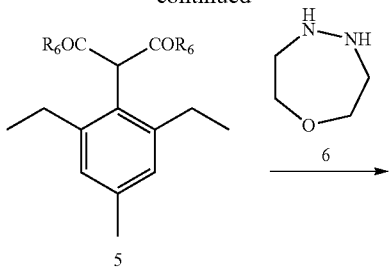

5

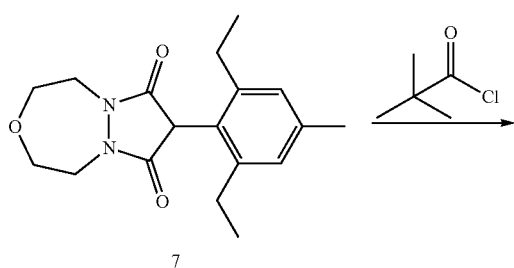

7

16
-continued

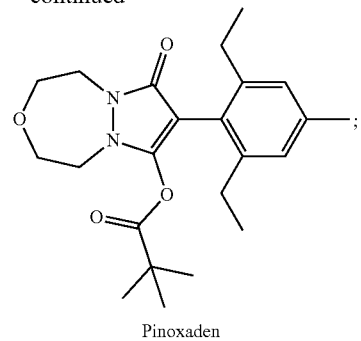

Pinoxaden wherein the catalyst A is selected from the group consisting of an organic acid, an organic base, an inorganic base and a mixture thereof; and the catalyst B is a metal catalyst;

wherein $R^6$ is selected from the group consisting of hydrogen, a $C_1$-$C_{10}$ alkyl group, a $C_1$-$C_{10}$ alkoxy group, a $C_6$-$C_{12}$ aryloxy group, a $C_1$-$C_{10}$ alkylamino group, a $C_6$-$C_{12}$ arylamino group, a di($C_1$-$C_{10}$ alkyl) amino group, a ($C_1$-$C_{10}$ alkyl)($C_6$-$C_{12}$ aryl) amino group, a di($C_6$-$C_{12}$ aryl) amino group, a $C_6$-$C_{12}$ arylgroup and a heteroaryl group containing one or two atoms selected from nitrogen, oxygen and sulfur.

\* \* \* \* \*